(12) United States Patent
Otsubo et al.

(10) Patent No.: US 6,827,804 B2
(45) Date of Patent: Dec. 7, 2004

(54) PROCESS FOR CONTINUOUSLY MAKING PANTS-TYPE DIAPER

(75) Inventors: Toshifumi Otsubo, Kagawa-ken (JP); Hiroki Yamamoto, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 318 days.

(21) Appl. No.: 10/093,696

(22) Filed: Mar. 11, 2002

(65) Prior Publication Data

US 2002/0129888 A1 Sep. 19, 2002

(30) Foreign Application Priority Data

Mar. 15, 2001 (JP) .......................................... 2001-074711

(51) Int. Cl.⁷ .......................... A61F 13/15; B32B 31/00
(52) U.S. Cl. ........................ 156/161; 156/163; 156/164; 156/204; 156/229; 156/256; 156/264
(58) Field of Search ................................. 156/264, 256, 156/161, 163, 164, 229, 204

(56) References Cited

U.S. PATENT DOCUMENTS

| | | | |
|---|---|---|---|
| 4,917,746 A | | 4/1990 | Kons et al. |
| 5,147,487 A | * | 9/1992 | Nomura et al. ............ 156/164 |
| 5,330,598 A | * | 7/1994 | Erdman et al. ............ 156/164 |
| 5,389,173 A | * | 2/1995 | Merkatoris et al. ........ 156/164 |
| 5,858,151 A | * | 1/1999 | Igaue et al. ................ 156/164 |
| 5,879,500 A | * | 3/1999 | Herrin et al. .............. 156/204 |

FOREIGN PATENT DOCUMENTS

| | | |
|---|---|---|
| EP | 0048011 B1 * | 3/1982 |
| EP | 0 688 551 | 12/1995 |
| EP | 0 797 970 | 10/1997 |
| EP | 1 249 214 | 10/2002 |
| JP | 03-176053 A * | 7/1991 |

OTHER PUBLICATIONS

Japanese Patent Application No. 1991–139349A.
Japanese Patent Application No. 1997–224973A.

* cited by examiner

*Primary Examiner*—Jeff H. Aftergut
(74) *Attorney, Agent, or Firm*—Lowe Hauptman Gilman & Berner, LLP

(57) ABSTRACT

A process for making a pants-type diaper without generation of waste material. The pants-type diaper is composed of a body fluid absorbent pad member curved in a U-shape, a front waist member and a rear waist member extending around front and rear waist-halves, respectively. The front and rear waist members are obtained by feeding first and second elastic members in parallel to each other in a machine direction so as to describe substantially sinusoidal curves, respectively, securing these elastic members to one surface of a web fed in the machine direction and then transversely bisecting the web between the first and second elastic members. The first and second elastic members are symmetric to each other about a center line bisecting the web but phase-shifted with respect to each other in the machine direction by half a cycle of the substantially sinusoidal curve.

15 Claims, 7 Drawing Sheets

PROCESS FOR CONTINUOUSLY MAKING PANTS-TYPE DIAPER

BACKGROUND OF THE INVENTION

This invention relates to a process for continuously making a disposable pants-type diaper.

Japanese Patent Application No. 1991-139349A discloses a process for continuously making a disposable pants-type diaper having a pair of elastically stretchable leg-holes. This process of well known art comprises the steps of: continuously feeding two elastic members spaced from each other in the direction orthogonal to the machine direction and securing them to one surface of a web continuously fed into the machine direction so that these two elastic members are opposed to each other with a region destined to define respective leg-openings therebetween; and cutting the web in conformity with the expected configuration of the leg-openings to form the leg-openings provided along peripheral edge regions thereof with the elastic members.

Japanese Patent Application No. 1997-224973A also discloses a process for continuously making a disposable diaper having a pair of elastically stretchable leg-holes. This process of well known art comprises the steps of: continuously feeding a web in a machine direction and securing two strips of continuous running elastic members in the machine direction so as to describe substantially sinusoidal curve of to one surface of the web; cutting the web along the curve of the strips delineated by these elastic members between these two streaks of the elastic members into upper and lower parts; separating these two portions of the web hereafter called web halves to the direction orthogonal to the machine direction by a desired dimension and then shifting one of the web halves separated to the machine direction by the distance corresponding to half a cycle of the substantially sinusoidal curve; and bonding these web halves in such regions as overlapping each other. In the web halves bonded in this manner, edges extending in the machine direction so as to describe substantially sinusoidal curves in which each pair of crest and trough opposed to each other define leg-opening. The leg-opening is provided along its peripheral edge region with the elastic members.

The process for making a diaper disclosed in the Japanese Patent Application No. 1991-139349A is adapted to form the leg-openings of the diaper by cutting out parts of the web. Consequently, pieces of waste material each having a shape in conformity with each leg-opening are inevitably generated, so labor and cost are required for disposal of these pieces of the waste material.

With the process for making the diaper disclosed in the Japanese Patent Application A No. 1997-224973, the web halves running in parallel to each other must be shifted twice, i.e., in the machine direction and in the direction orthogonal to the machine direction. Control of the process is correspondingly complicated and it becomes difficult to improve the productivity.

SUMMARY OF THE INVENTION

It is an object of this invention to provide a process for making a pants-type diaper having elastically stretchable leg-openings improved so that generation of waste material from web can be minimized and a frequency of shifting the running web can be also minimized.

According to this invention, there is provided a process for continuously making a pants-type diaper having a body fluid absorbent pad member curved in a U-shape along a crotch region and extending into front and rear waist regions, a sheet-like front waist member attached to an outer surface of the pad member in the front waist region so as to cover a half of the waist region in circumferential direction hereafter called waist half and a sheet-like rear waist member attached to the outer surface of the pad member in the rear waist region so as to cover another waist half in the circumferential direction wherein respective transversely opposite side edge regions of the front and rear waist members are joined together to form a circular waist region and cooperate with the pad member to define a pants-shape.

The process further comprises the steps of:

a. continuously feeding a single web destined to form the front and rear waist members in a machine direction and, at the same time, continuously feeding under extension a first elastic member extending in a machine direction so as to describe half a cycle of a substantially sinusoidal curve within a length corresponding to each of the waist halves being consecutive in the machine direction and securing this first elastic member to one surface of the web using an adhesive while a second elastic member being symmetric to the first elastic member about a center line bisecting a width of the web in a direction orthogonal to the machine direction is continuously fed so as to describe a curve phase-shifted with respect to the first elastic member by a half cycle and to be adjacent to the first elastic member in the orthogonal direction and secured to the one surface of the web using the appropriate adhesive, and thereby forming a composite web;

b. cutting the first composite web between the first and second elastic members so as to bisect this composite web in the orthogonal direction and separating them from each other by a predetermined dimension in the orthogonal direction to form first and second web halves running in parallel to each other in the machine direction;

c. placing, substantially in a middle of the length corresponding to the half cycle of the front waist region in the machine direction, a body fluid absorbent solid pad member extending in the orthogonal direction and having a dimension in the machine direction being shorter than the length of the half cycle upon each pair of the first web half and second web half to bridge and joining them to these web halves to form a first series of diapers running in the machine direction;

d. folding back, in the orthogonal direction, the first series of diapers along a center line dividing the first series of diapers into upper and lower parts with the pad member inside so as to form a second series of diapers;

e. joining each pair of the first and second web halves placed upon each other in the second series of diapers together substantially in the middle of each pair of the adjacent pad members to form joining regions arranged intermittently in the orthogonal direction between each pair of the adjacent pad members; and f. cutting the second series of diapers along a cutting line extending in the orthogonal direction through one of the joining regions and in a vicinity of the joining regions to obtain an individual diaper having the first and second web halves joined together along both side edges of the pad member.

The process according to this invention for continuously making the disposable diaper enables the front and rear waist members to be obtained merely by transversely bisecting, along the substantially sinusoidal curve, the web continuously fed in the machine direction and then moving the respective web halves away from each other in the direction of cd. Accordingly, no waste material is generated and such troublesome work as the treatment of waste material is not required. Furthermore, the process is simplified in comparison to the conventional process by the prior art and easily controlled. As a result, productivity of the diaper is correspondingly enhanced.

DETAILED DESCRIPTION OF THE PREFERRED EMBODIMENTS

Details of a process according to this invention for continuously making a disposable pants-type diaper will be more fully understood from the description given hereunder in reference to the accompanying drawings.

Figure 1:
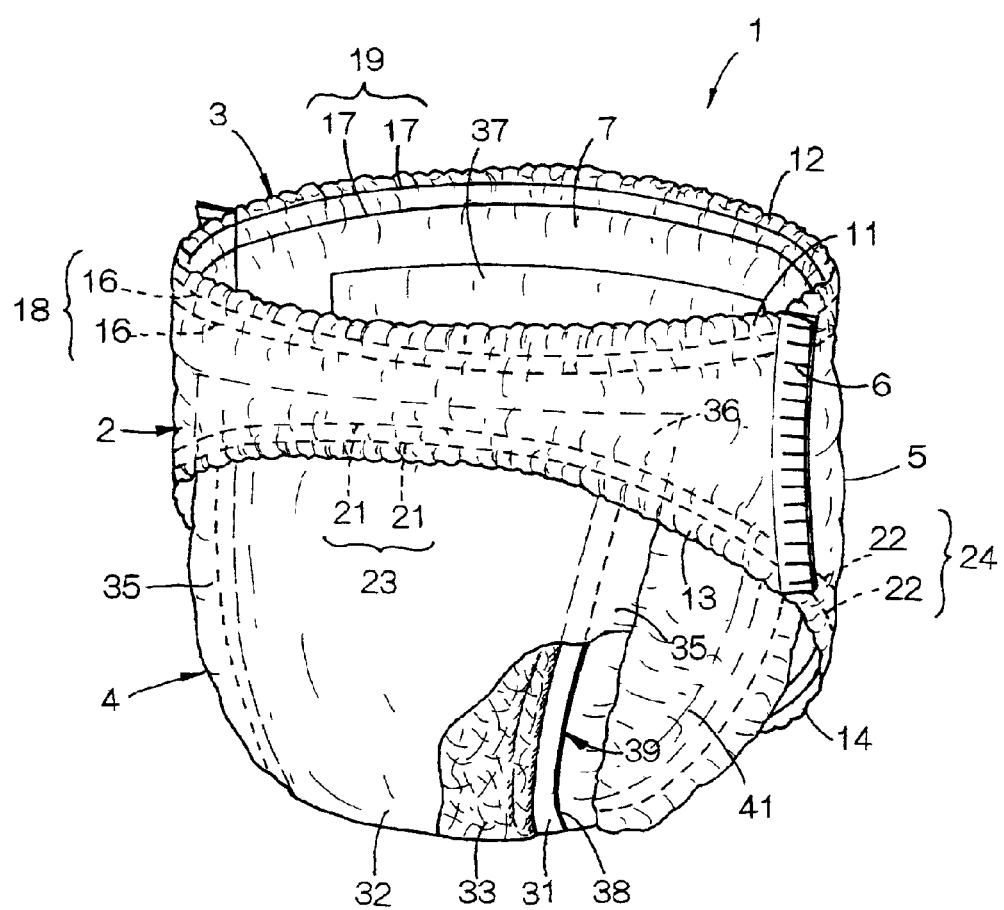
FIG. 1 is a partially cutaway perspective view showing the diaper.

FIG. 1 is a perspective view showing a disposable pants-type diaper 1 by the process according to this invention for continuously making the disposable pants-type diaper. The diaper 1 is composed of a front waist member 2 lying on a front waist region, a rear waist member 3 lying on a rear waist region and a body fluid absorbent pad member 4 curved in a U-shape so as to lie on a crotch region. The front and rear waist members 2, 3 are made of a nonwoven fabric and extend along respective waist-halves. Transversely opposite side edge regions of the one waist half are overlaid upon one of the transversely opposite side edge regions of other waist half in zones 6 and bonded together along the respective side edge regions intermittently in vertical direction so as to form an annular waist region 5 and a waist-opening 7. The front and rear waist members 2, 3 respectively have upper edge regions 11, 12 and lower edge regions 13, 14. The front and rear upper edge regions 11, 12 are provided on the inner surfaces thereof with front and rear side upper elastic members 18, 19 each comprising a plurality of elastic threads 16, 17. These members 18, 19 are secured under extension with the respective upper edge regions 11, 12 so that these members 18, 19 may become contiguous to each other and thereby encircle the waist-opening 7. The lower edge regions 13, 14 are provided on the inner surfaces thereof with front and rear lower elastic members 23, 24. These front and rear side lower elastic members 23, 24 each comprising a plurality of elastic strings 21, 22 are secured under extension with the lower edge regions 13, 14 on the inner surface thereof.

The pad member 4 comprises a liquid-pervious topsheet 31 facing a wearer's skin of the diaper 1, a backsheet 32 facing away from the wearer's skin and a body fluid absorbent core 33 interposed between these two sheets 31, 32. The top- and backsheets 31, 32 extend outwardly beyond transversely opposing peripheral edges of the core 33 and overlaid and joined to each other in the respective fringes so as to form a pair of side edge flaps 35 extending outwardly from the transversely opposite side edges of the core 33. The pad member 4 curved in a U-shape has a front upper end region 36 and a rear upper end region 37 of which the upper end region 36 is bonded to the inner surface of the front waist member 2 and another upper end region 37 is bonded to the inner surface of the rear waist member 3. In the side edge flaps 35, a pair of side edge elastic members 39 each comprising a single or plural elastic string(s) extending to an upper direction along to the side edges of the core 33 in a U-shape are bonded under extension to the inner surfaces of the top- and backsheets 31, 32. As shown, the pad member 4 of such arrangement intersects the lower edge regions 13, 14 of the front and rear waist regions 2, 3 in the vicinity of the side edge regions of the diaper 1 so as to form a pair of leg-openings 41 wherein the side edge elastic members 39 of the pad member 4 cooperate with the lower elastic members 23, 24 of the front and rear waist members 2, 3 to form leg surrounding elastic members of the diaper 1. On the transversely opposite side edge regions of the waist, the front and rear lower elastic members 23, 24 become substantially contiguous to each other to serve as a single elastic member and its periphery runs obliquely downward from the front side toward the rear side. The lower elastic member 24 serves to press the pad member 4 tightly upward against hip of the wearer of the diaper 1.

Figure 2:
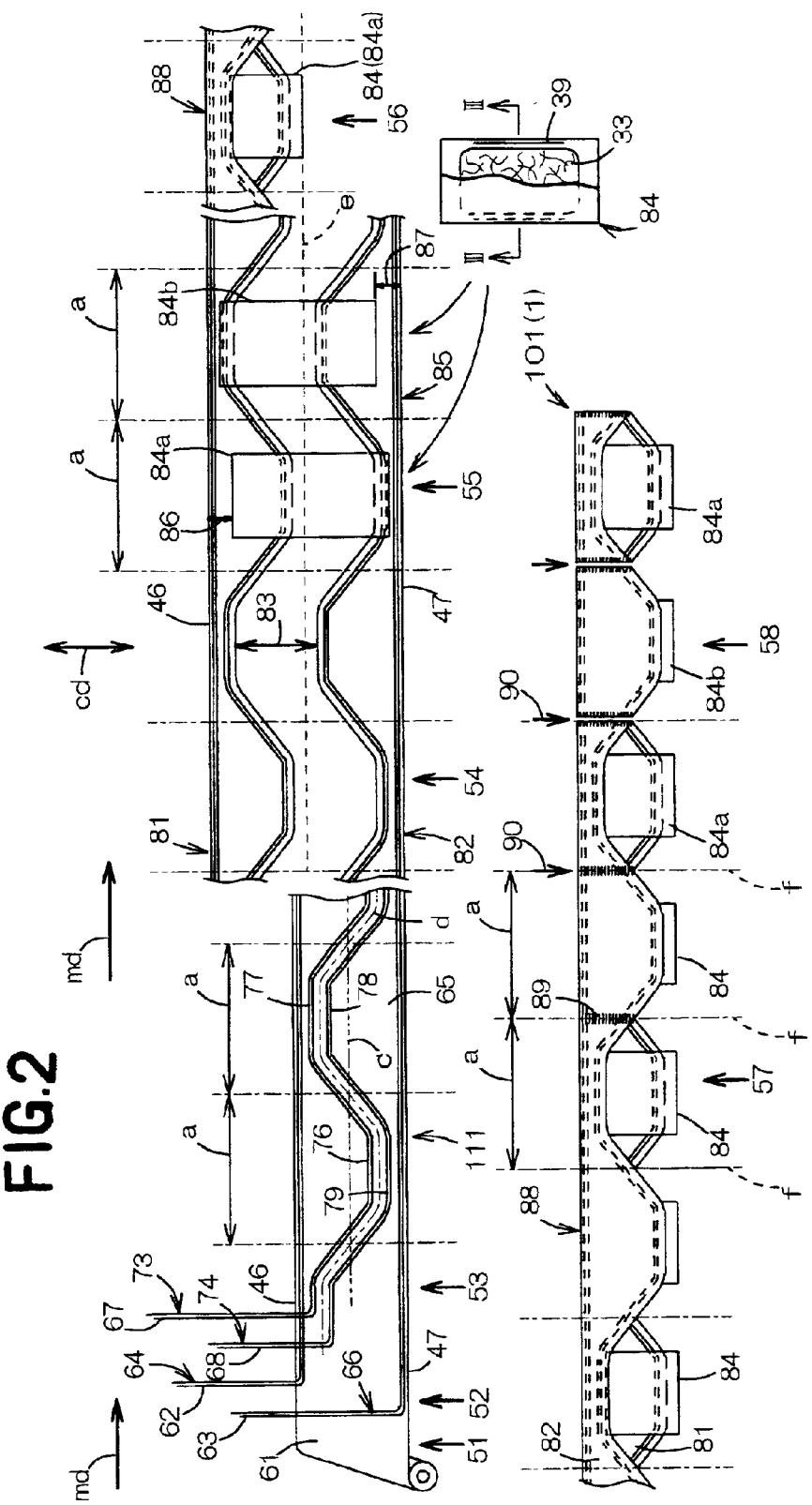
FIG. 2 is a diagram schematically illustrating a process for making the diaper.

FIG. 2 is a diagram schematically illustrating major steps of a process for making the diaper 1, in which a machine direction is indicated by an arrow md and a direction orthogonal to the machine direction is indicated by an arrow cd. The process is illustrated by eight steps from the first step 51 to the eighth step 58. In the first step 51, a single layer of web 61 is continuously fed into the machine in the direction of md from the left side as viewed in FIG. 2.

In the second step 52, waist-opening-surrounding elastic members 64, 66 each comprising a plurality of elastic strings 62, 63 are continuously fed onto transversely opposite side edge regions of the web 61, respectively, and secured to the upper surface of the web 61 by means of an adhesive (not shown). The adhesive may be applied to the elastic threads 62, 63 or to the web 61.

In the third step 53, a first elastic member 73 and a second elastic member 74 each comprising a plurality of elastic strings 67, 68, respectively, are continuously fed under a desired extension onto the upper surface of the web 61 so as to describe substantially a sinusoidal curve with its half a cycle a and secured thereto by means of an adhesive (not shown). In this way, composite web 65 is formed, which consists of the web 61 and the elastic members 64, 66, 74, 74. The first member 73 and the second elastic member 74 are symmetric each other about a center line c of the web 61 and phase-shifted with respect to each other in the direction of md by the distance corresponding to half the cycle a. In other words, if the first elastic member 73 is phase-shifted in the direction of md by half the cycle a as viewed in FIG. 2, trough 76 and crest 77 described by the first elastic member 73 will come in symmetric relationship with the corresponding crest 78 and trough 79 described by the second elastic member 74, respectively, about the center line c.

In the fourth step 54, the web 61 is cut along a line d bisecting a distance between the first elastic member 73 and the second elastic member 74 in the previous third step 53 to obtain first web half 81 and second web half 82. These web halves 81, 82 are moved away in the direction orthogonal to the direction md so as to be spaced from each other by a desired dimension 83.

In the fifth step 55, body fluid absorbent pad members 84 one of which is shown in FIG. 2 as partially cutaway are placed upon the first and second web halves 81, 82 to bridge them and regions of the pad member 84 overlapping the respective web halves 81, 82 are joined to them by means of an adhesive (not shown). In this way, a first series of diapers 85 is obtained. Each pad member 84 as measured in the direction of md is shorter in dimension than the length of half the cycle a. The pad member 84a, one of the pair of the pad members 84 adjacent in the direction of md is centered on the trough 76 described by the first elastic member 73 and the crest 79 described by the second elastic member 74 while the other pad member 84b is centered at the crest 77 described by the first elastic member 73 and the crest 78 described by the second elastic member 74. In these adjacent pad members 84a and 84b, the distance 86 from the side edge 46 of the web 61 to the pad member 84a is equal to the distance 87 from side edge 47 of the web 61 to the pad member 84b. While the pad member 84 actually comprises the body fluid absorbent core 33 and the elastic members 39 provided in the vicinity of transversely opposite side edge regions of the core 33 (See FIG. 3), FIG. 2 illustrates only external shape of the pad member 84 placed on the web 61. The first and second web halves 81, 82 as well as the first and second elastic members 73, 74 underlying the member 84 are shown by imaginary lines to indicate the presence of them.

In the sixth step 56, the first series of diapers 85 is folded back along a center line e bisecting the width thereof with the pad members 84 inside to obtain a second series of diapers 88.

In the seventh step 57, the first and second web halves 81, 82 placed upon each other are joined together in a region 89 vertically extending about a center line f bordering each pair of the adjacent pad members 84, 84 in the second series of diapers 88.

In the eighth step 58, the second series of diapers 88 is cut in regions indicated by arrows 90, i.e., along the respective center lines f so that the respective regions 89 are bisected into right and left halves and thereby individual diapers 101 are obtained. As will be obviously understood from FIG. 2, the individual diapers are obtained one for every half the cycle of the first and second elastic members 73, 74 respectively describing the substantially sinusoidal curves. As the second series of diapers 88 are cut along the center lines f, the forward-oriented diapers 101 respectively having the pad members 84a and the rearward-oriented diapers 101 respectively having the pad members 84b are alternately obtained. However, these diapers 101 are different merely in the orientation in the course of production and really identical one to another. In every individual diaper 101, the elastic members 64, 66 associated with the waist-opening are placed upon each other while the first and second elastic members 73, 74 are placed upon each other along the joining regions 89.

The diaper 101 obtained upon completion of these steps corresponds to the diaper 1 shown in FIG. 1 and the pad member 84 corresponds to the pad member 4 of the diaper 1. In the diaper 101 having the pad member 84a, the first web half 81 and the second web half 82 respectively define the rear waist member 3 and the front waist member 2 of the diaper 1. In this case, the elastic members 64 and 66 both associated with the waist-opening respectively define the rear side upper elastic member 19 and the front side upper elastic member 18 of the diaper 1. The first and second elastic members 73, 74 respectively define the rear side lower elastic member 24 and the front side lower elastic member 23 of the diaper 1. In the diaper 101 having the pad member 84b, the first web half 81 and the second web half 82 respectively define the front waist member 2 and the rear waist member 3 of the diaper 1. In this case, the elastic members 64 and 66 both associated with the waist-opening respectively define the front side upper elastic member 18 and the rear side upper elastic member 19 of the diaper 1. The first and second elastic members 73, 74 respectively define the front side lower elastic member 23 and the rear side lower elastic member 24 of the diaper 1.

A material for the web 61 used to implement the process according to this invention may be selected from a group of materials including a nonwoven fabric, a plastic film and a composite sheet consisting of nonwoven fabric and plastic film. The web 61 may be liquid-impervious or breathable and liquid-impervious or liquid-pervious.

Figure 3:
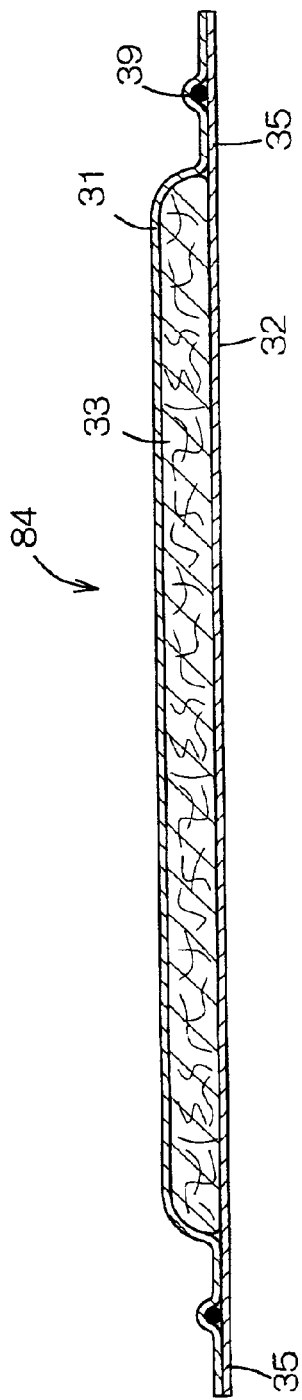
FIG. 3 is a cross-sectional view showing the pad member taken along a line III—III in FIG. 2.

FIG. 3 is a cross-sectional view of the pad member 84 taken along a line III—III in FIG. 2. The pad member 84 is identical to the pad member 4 of FIG. 1 and comprises the liquid-pervious topsheet 31, the liquid-impervious backsheet 32 and the body fluid absorbent core 33 disposed between these two sheets 31, 32. In the pair of flaps 35 formed outside the transversely opposite side edges of the core 33, the side edge elastic members 39 are disposed under extension between the top- and backsheets 31, 32. The topsheet 31 may be formed by a nonwoven fabric or finely apertured plastic film and the backsheet 32 may be formed by a plastic film.

Figure 4:
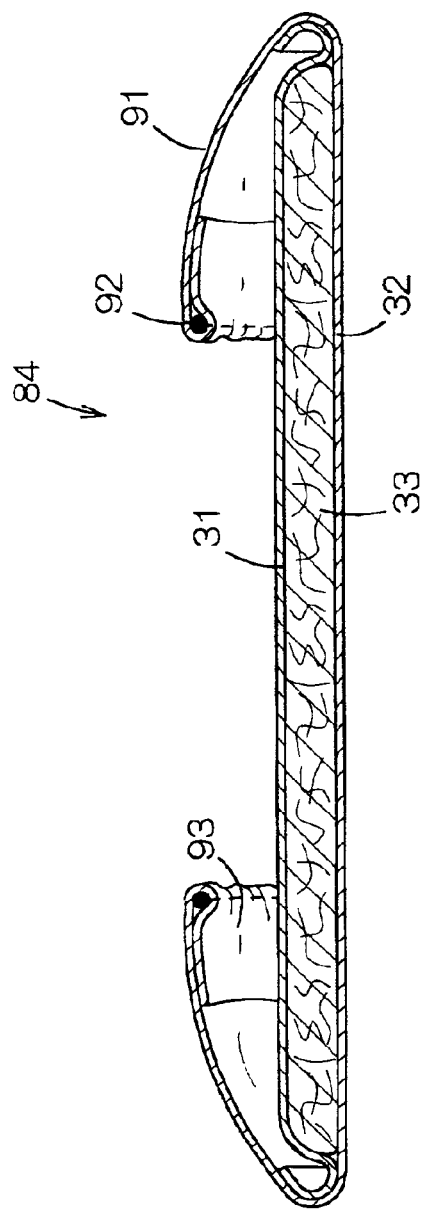
FIG. 4 is a view similar to FIG. 3 but showing another embodiment of the pad member.

FIG. 4 is a view similar to FIG. 3 but showing another embodiment of the pad member 84. In this pad member 84, the top- and backsheets 31, 32 extend outwardly beyond the transversely opposite side edges of the core 33 and the backsheet 32 extends outwardly further beyond transversely opposite side edges of the topsheet 31. Such further extension 91 of the backsheet 32 is folded back inwardly of the pad member 83. The extension 91 is provided along its inner edges with elastic members 92 extending in the direction cd in FIG. 2 and bonded under extension thereto. While not shown, inner surface of the extension 91 is bonded to the topsheet 31 at its respective opposite end regions as viewed in the direction cd in FIG. 2 so as to form pockets 93 opening inwardly of the pad member 84. A portion of body fluids tending to flow sideways with respect to the pad member 84 flows into these pockets 93 and is effectively prevented from flowing sideways from the pad member 84.

Figure 5:
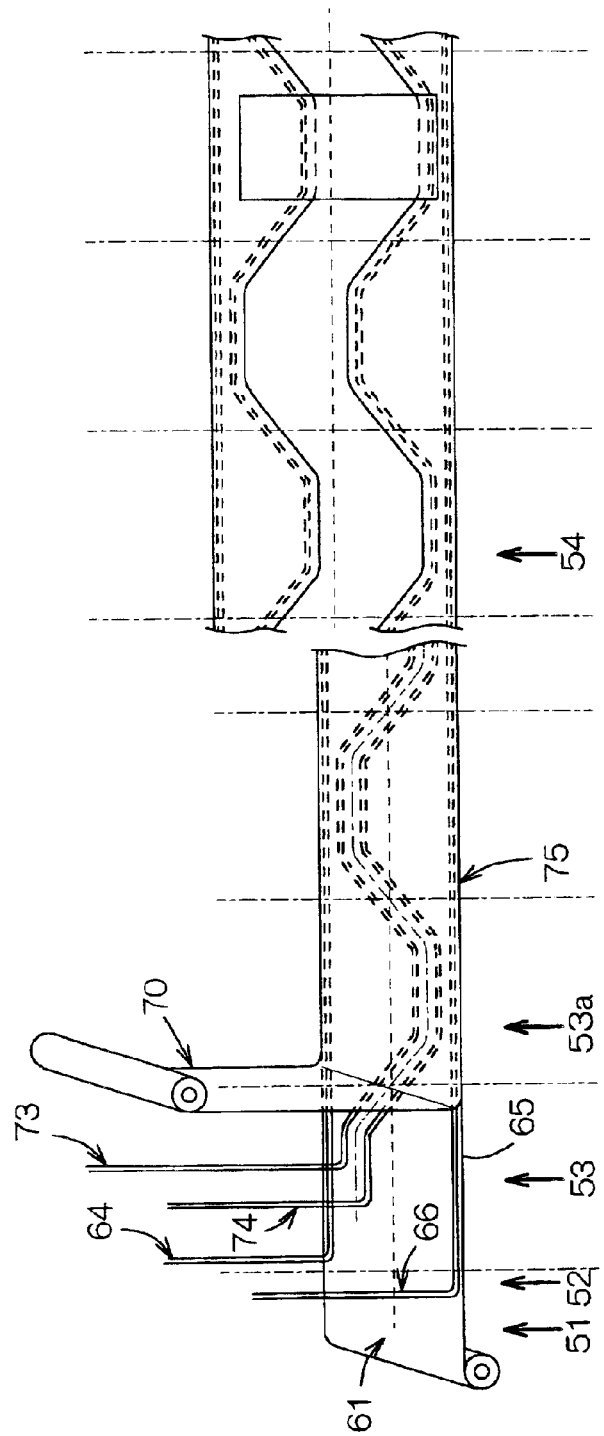
FIG. 5 is a partial diagram schematically illustrating another embodiment of the process for making the diaper.

FIG. 5 is a view similar to FIG. 2 but illustrating another embodiment of the process according to this invention. According to this embodiment of the process illustrated in FIG. 5, in the second and third steps 52, 53, the respective elastic members 64, 66, 73, 74 are secured to the web 61 fed in the first step 51 to form the composite web 65. Then, in an additional step 53a, a second web 70 is fed from above the respective elastic members 64, 66, 73, 74 and joined to the composite web 65 to obtain a second composite web 75. This second composite web 75 is subjected to the fourth–eighth steps 54–58 to form the individual diapers 101. The second web 70 may be made of a nonwoven fabric or plastic film. The diaper 101 obtained using this embodiment of the process improves a touch of the diaper since the respective elastic members 64, 66, 73, 74 are not in contact with the wearer's skin when the diaper 101 is worn.

Figure 6:
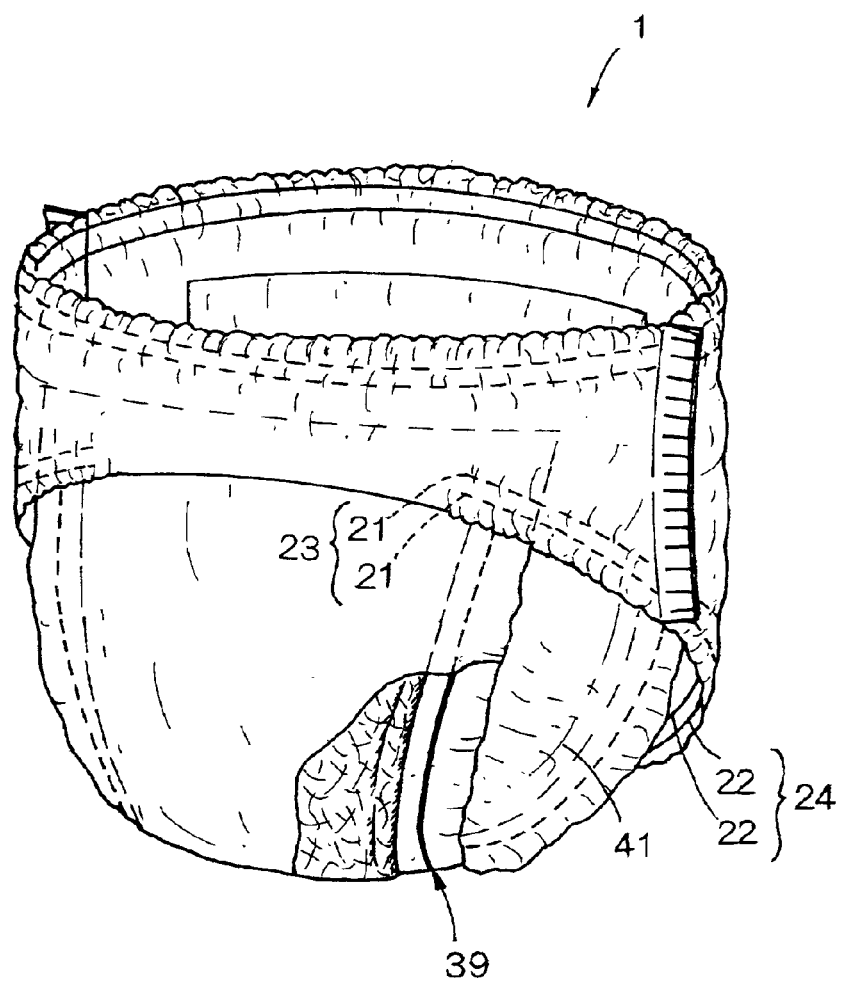
FIG. 6 is a partially cutaway perspective view similar to FIG. 1 but showing another embodiment of the diaper.

FIG. 6 shows another embodiment of a pants-type diaper 1 obtained using the process according to this invention described just above. This diaper 1 is similar to the diaper 1 in FIG. 1 in an external shape but distinguished from the latter in that the front side lower elastic member 23 comprising a plurality of elastic threads 21 and the rear side lower elastic member 24 comprising a plurality of elastic strings 22 respectively lie only along peripheral edge regions of left and right leg-openings 41 instead of circumferentially extending along the respective waist halves as in FIG. 1. Thus, these lower elastic members 23, 24 cooperate with the side edge elastic members 39 to form the elastic members associated with the respective leg-openings. Such diaper 1 presents its external appearance different from that of the diaper 1 shown in FIG. 1 due to the absence of the lower elastic members 23, 24 in middle zones of both the front waist side and the rear waist side.

Figure 7:
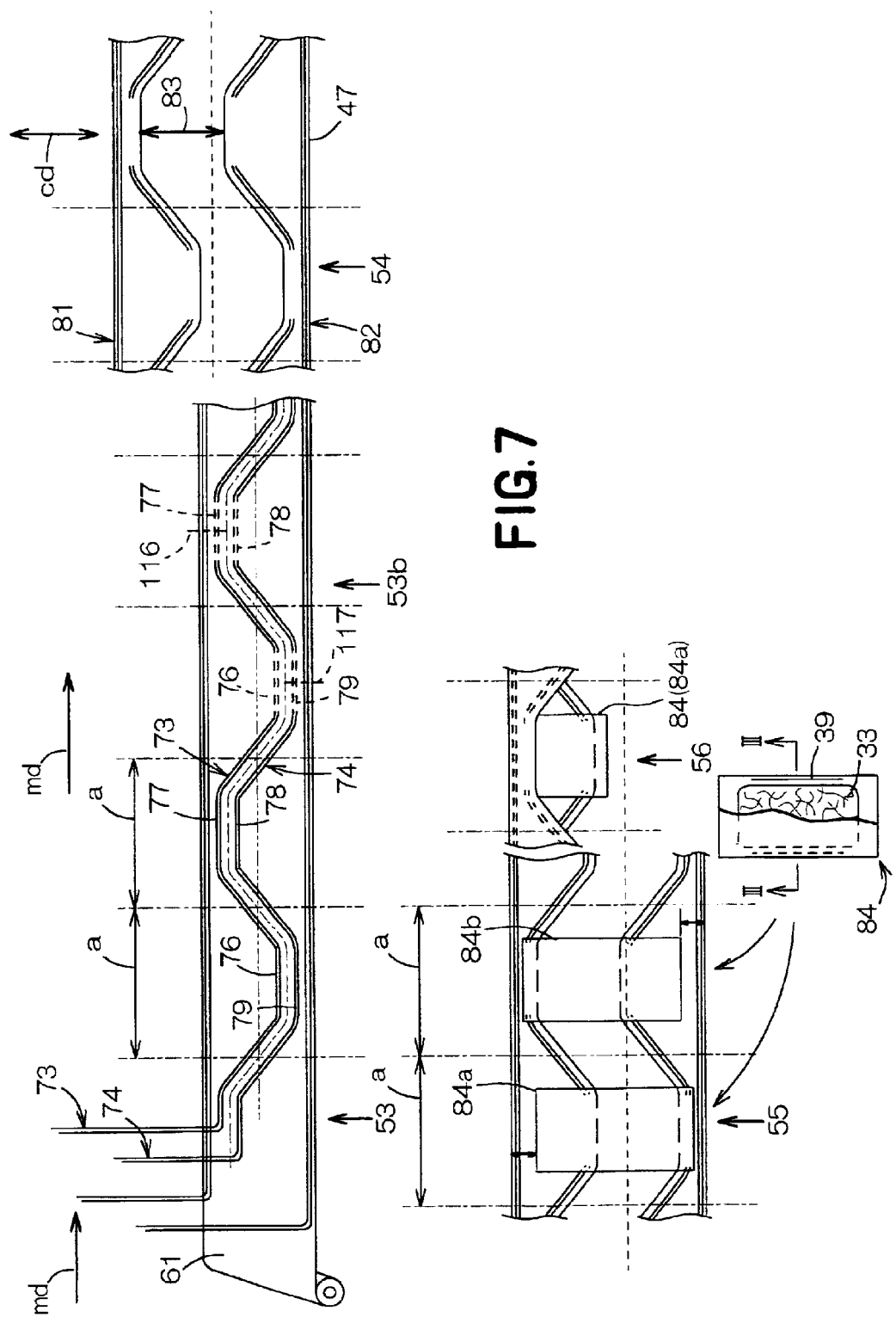
FIG. 7 is a partial diagram schematically illustrating the process for making the diaper of FIG. 6.

FIG. 7 is a diagram partially illustrating the process for making the diaper 1 in FIG. 6. The stock materials as have been described above are subjected to, in addition to the steps illustrated in FIG. 2, an additional step 53b provided between the third step 53 and the fourth step 54 of FIG. 2 to obtain the diaper 1. In the additional step 53b, most portions of the troughs 76 and the crests 77 of the first elastic member 73 as well as the crests 78 and the troughs 79 of the second elastic member 74 indicated by chain lines are cut off and portions of these elastic members 73, 74 indicated by solid lines remain on the web 61. In order that operation of cutting away can be easily performed, the troughs 76 and the crests 77 of the first elastic member 73 as well as the crests 78 and the troughs 79 of the second elastic member 74 are not substantially secured to the web 61 in the third step 53 in FIG. 2. While the first and second elastic members 73, 74 may be cut off together with the portions of the web 61 underlying these elastic members 73, 74, operation of cutting may be confined to the first and second elastic members 73, 74 only to reduce the quantity of the waste generated associated with cutting. Instead of cutting them in a manner as has been described, it is also possible to cut the troughs 76 and the crests 77 of the first elastic member 73 as well as the crest 78 and the troughs 79 of the second elastic member 74 along lines 116, 117 bisecting them in the direction of md and then to let them contract. Assumed that the first elastic member 73 is under extension along its troughs 76 and crests 77 and the second elastic member 74 is under extension along its crests 78 and troughs 79, the diaper 1 in FIG. 6 can be obtained merely by cutting these members 73, 74 and then leaving them contract. In this way, the first and second elastic members 73, 74 or the web 61 do not generate the waste at all.

As will be apparent from the foregoing description, the process according to this invention allows the first and second elastic members 73, 74 to be cut off or divided along desired portions so that the diaper 1 having only one of the front side lower elastic member 23 and the rear side lower elastic member 24 may be made, instead of the diaper 1 as shown in FIG. 6.

In the process according to this invention of which the preferred embodiments are illustrated, the elastic members 64, 66 associated with the waist-opening may be fed after the first and second elastic members 73, 74 have been fed. It is possible to implement the process according to this invention without the step of feeding the elastic members 64, 66 associated with the waist-opening. The shapes of every half the cycle of the substantially sinusoidal curve described by the first and second elastic members 73, 74 may be symmetric or asymmetric to each other. When the first and second web halves 81, 82 are joined together in the regions 89, it is also possible to use two separate bonding lines extending in the direction of cd with the center line f therebetween. In this case also, the second series of diapers 88 is divided along the respective center lines f. The process according to this invention enables the diaper to be continuously made at a high speed. This process is suitable for making the disposable diaper always exposed to severe price competition.

What is claimed is:

1. A process of continuously making pants-type diapers, said method comprising the steps of:

feeding a web in a machine direction;

cutting said web along a cutting line having a wave form longitudinally extending in said machine direction, thereby dividing said web in a cross direction transverse to said machine direction into a first web half and a second web half;

moving said first web half away from said second web half by a predetermined distance in said cross direction without shifting said first web half and said second web half relative to each other in said machine direction;

after said moving, placing a plurality of body fluid absorbent pad members on said first web half and said second web half to bridge between said first web half and said second web half;

joining said pad members to said first web half and said second web half;

folding said pad members along a folding line extending in the machine direction, thereby placing said first and second web halves one upon another;

bonding said first web half to said and second web half, that have been placed one upon another, in bonding regions between adjacent said pad members; and cutting said web in said cross direction in said bonding regions to obtain individual diapers.

2. The process of claim 1, further comprising the step of continuously feeding a first elastic member on said web so that said first elastic member describes a first curve having a first wave form longitudinally extending in said machine direction.

3. The process according to claim 2, further comprising the step of continuously feeding a second elastic member on said web so that said second elastic member extends in said machine direction and describes a second curve having a second wave form;

wherein said cutting line is located between said first and second curves, and said cutting line, said first curve and said second curve do not cross each other.

4. The process according to claim 3, further comprising the step of securing said first and second elastic members to said web.

5. The process according to claim 3, wherein said first and second curves would be symmetric with respect to a center line bisecting a width of said web measured in the cross direction if said second curve was shifted in the machine direction with respect to said first curve by a half cycle of the first wave form of said first curve.

6. The process according to claim 2, further including the step of removing said first elastic member in regions underlying said pad members.

7. The process according to claim 2, further comprising the steps of continuously feeding another web so that said first elastic member is sandwiched between said web and said another web, and bonding said another web to said web.

8. The process according to claim 1, further including the step of securing an elastic element under extension to an edge region of said web, said elastic element extending in the machine direction.

9. The process according to claim 1, wherein each of said pad members comprises a liquid-pervious topsheet, a liquid-impervious backsheet and a liquid-absorbent core disposed between said topsheet and backsheet, and has transversely opposite side edge regions that extend in said cross direction and are provided with elastic elements having a stretchability in said cross direction.

10. The process according to claim 8, wherein, in said placing step, said pad members are arranged relative to each other in a staggering manner.

11. A process of continuously making pants-type diapers, said method comprising the steps of:
   a. forming a composite web by
      continuously feeding a web in a machine direction,
      continuously feeding a first elastic member under extension so that said first elastic member extends in said machine direction and describes a first, substantially sinusoidal curve,
      securing said first elastic member to one surface of said web by adhesive,
      continuously feeding a second elastic member to describe a second curve, wherein said first and second curves would be symmetric with respect to a center line bisecting a width of said web measured in a cross direction orthogonal to said machine direction if said second curve was phase-shifted with respect to said first curve by a half cycle of said first curve, and
      securing said second elastic member to said surface of said web by adhesive;
   b. cutting said composite web between said first and second elastic members so as to bisect said composite web in said cross direction to form a first web half and a second web half, and separating said first web half from said second web half by a predetermined distance in said cross direction without shifting said first web half and said second web half relative to each other in said machine direction;
   c. placing, a plurality of body fluid absorbent pad members on said first web half and said second web half to bridge between said first web half and said second web half, and bonding said pad members to said first web half and said second web half to form a first series of diapers;
   d. folding, in said cross direction, said first series of diapers along a center line of said first series of diapers so as to form a second series of diapers having said pad members therein;
   e. intermittently bonding said first web half to said second web half, that have been placed upon each other in said second series of diapers, in joining regions between adjacent said pad members; and
   f. cutting said second series of diapers in said cross direction through one of said joining regions and in a vicinity of said joining regions to obtain individual diapers.

12. The process according to claim 11, further including the step of securing an elastic element under extension to one of said web and said composite web along an edge region thereof, said elastic element extending in the machine direction.

13. The process according to claim 11, further including the step of cutting off or dividing at least one of said first and second elastic members at determined regions thereof.

14. The process according to claim 11, wherein each of said pad members comprises a liquid-pervious topsheet, a liquid-impervious backsheet and a liquid-absorbent core disposed between said topsheet and backsheet, and has transversely opposite side edge regions that extend in said cross direction and are provided with elastic elements having a stretchability in said cross direction.

15. The process according to claim 11, wherein step a) further comprises the steps of
   feeding another web from above said first and second elastic members, and
   bonding said another web onto said surface of said web using adhesive.

* * * * *